United States Patent [19]

Anthony et al.

[11] Patent Number: 5,058,444
[45] Date of Patent: Oct. 22, 1991

[54] SYSTEM FOR ANALYZING ENTRAINED SOLIDS SUCH AS COTTON OR SEED

[75] Inventors: William S. Anthony, Greenville; Oliver L. McCaskill, Leland, both of Miss.

[73] Assignee: The United States of America as represented by the Secretary of Agriculture, Washington, D.C.

[21] Appl. No.: 514,478

[22] Filed: Apr. 25, 1990

[51] Int. Cl.$^5$ ............................................. G01N 1/00
[52] U.S. Cl. ..................................... 73/866; 73/863.21
[58] Field of Search ..................... 73/866, 863, 863.01, 73/863.41, 863.51, 863.54, 863.81–863.86, 863.21, 863.11, 863.12, 864.81, 863.71, 865.5, 160, 823.21; 250/341, 358.1, 369.1, 360.1; 356/36, 237, 245; 19/105, 97.5, 150, 157, 296, 161.1, 205, 300, 303; 100/99

[56] References Cited

U.S. PATENT DOCUMENTS

| | | | |
|---|---|---|---|
| 2,353,828 | 7/1944 | Hyde | 73/863.21 |
| 2,931,076 | 4/1960 | Clark | 19/205 |
| 3,138,029 | 6/1964 | Rich | 73/865.5 |
| 4,485,684 | 12/1984 | Weber et al. | 73/863.12 |
| 4,777,702 | 10/1988 | Jung et al. | 19/205 |

Primary Examiner—Robert Raevis
Attorney, Agent, or Firm—M. Howard Silverstein; John D. Fado

[57] ABSTRACT

A closed loop system is provided for by-passing, from a duct, a small fluid-entrained stream of particulates or solids; separating the stream into a particulate fraction and a fluid stream that essentially is free of the particulates; returning such fluid stream to the duct downstream from the by-pass; analyzing the particulate fraction; and dispersing particulates, after analysis, into the fluid stream being returned to the duct. To analyze particulates such as cotton lint, the separated lint is formed into a batt, the batt is passed in contact with a wall having an analyzer operatively associated therewith; a segment of the batt is compressed against the wall adjacent the analyzer by placing a weighted object against the segment; analysis is carried out on the compressed segment after which the object is lifted off the segment to permit the segment to be displaced with another segment of the batt; and the compression, analyzing, and lifting steps are repeated on the second segment.

19 Claims, 4 Drawing Sheets

FIG.4
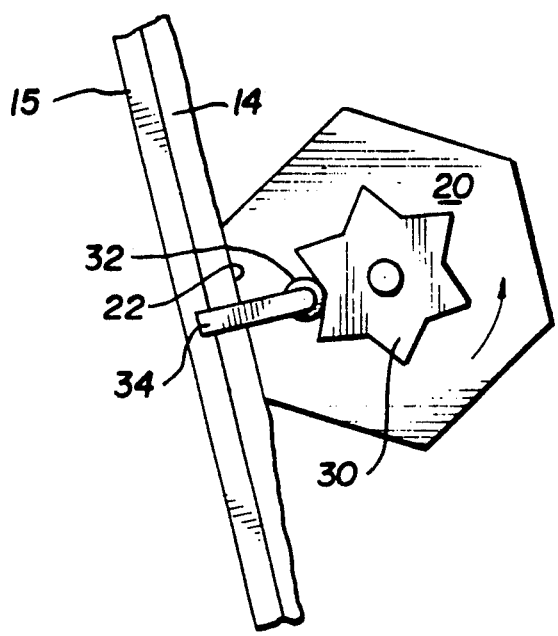
FIG.4a
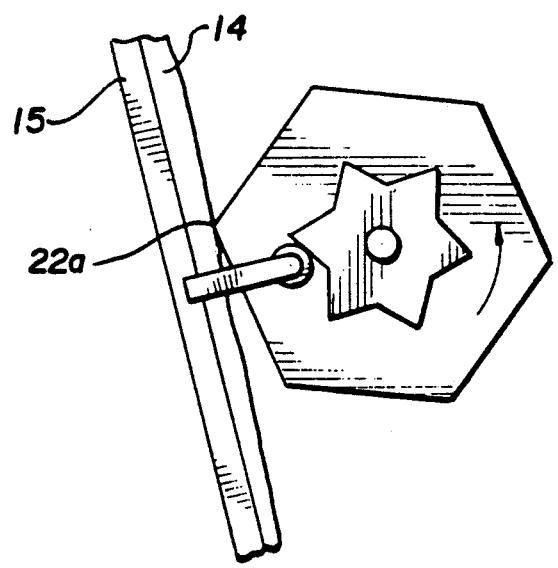
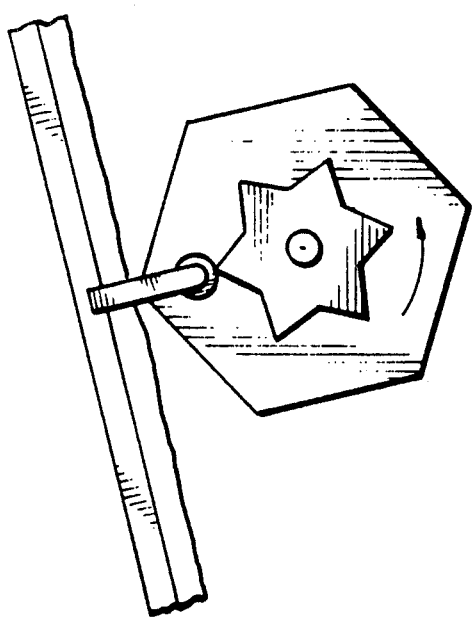
FIG.4b

SYSTEM FOR ANALYZING ENTRAINED SOLIDS SUCH AS COTTON OR SEED

The present invention relates to analyzing flowable solids such as cotton passing through a gin.

PRIOR ART

Presently there is no known system for analyzing cotton for properties such as color, trash or moisture content as it flows through a gin in an air-entrained state.

SUMMARY

Generally, the invention comprises a duct having fluid-entrained solids (or particulates) passing therethrough; by-pass means connected to the duct to remove a fluid stream containing a small part of the solids in the duct; means to separate the stream into a solids fraction and a fluid stream that essentially is free of the solids; means to direct the essentially solids-free fluid stream back to the duct downstream from the by-pass means; means to analyze the solids fraction; and means to disperse solids, after analysis, into the fluid stream being directed back to the duct.

The analyzing means comprises:

a. means to pass a layer of the separated solids fraction (which may consist of cotton particulates or other flowable solids) in contact with a wall having a pressing zone thereon;

b. means to press a segment of the solids fraction against the wall in the pressing zone, by placing a weighted object on the segment;

c. a solids analyzer operatively associated with the pressing zone, that analyzes the solids fraction segment when pressed against the wall in the pressing zone;

d. means to lift the weighted object off the wall after analysis so that another segment of the solids fraction may displace the first segment in the pressing zone, and thereby may be pressed and analyzed in turn.

In those instances where the layer consists of a batt of cotton lint, the pressure is applied with sufficient force so that the compressed batt segment presents a face of uniform cotton density against the wall, wherein the uniform density is sufficient to enable the batt segment to be accurately analyzed by means such as optical or infrared scanners for at least one of the following properties: color, trash content, moisture content.

As used in the specification and claims, the phrase, "a face of uniform cotton density", in reference to the layer or batt of cotton being pressed against the wall, means that the face of the layer which is pressed against the wall essentially is filled with cotton and impurities, with no voids. In other words, the layer is sufficiently compressed so that its face in contact with the wall essentially is completely occupied by cotton and impurities. This enables an optical or other analyzer adjacent the wall to make an analysis thereof, through, for example, a lens or window in the wall, which measurement is an accurate reflection of such properties of the layer as color, trash content, and moisture content.

In the case of cotton, ordinarily the process is carried out in a cyclical or intermittent manner on a series of batt segments; and the batt flows by gravity down the wall. The batt usually is formed by condensing air-entrained lint cotton into a batt.

The weighted object that compresses the batt segment comprises a member having at least one surface that conforms to the shape of the wall so as to be able to lie in substantially parallel, pressing engagement with the layer or batt on the wall. Lifting means are provided to cyclically lift the member off the batt segment, so as to permit another batt segment to displace the previously analyzed segment.

An object of the present invention is to provide a closed loop, solids entrainment system for removing, analyzing, and returning entrained particulates or solids from and to a processing system, such as a ginning system, wherein part of the entrainment medium flowing through the processing system is employed to convey the solids to the analyzer, and thereafter is employed to return analyzed solids to the processing system.

Another object is to provide uniform cotton density on a face of a cotton layer or batt to enable immediate and increased accuracy of analysis to be performed thereon, including color (e.g., yellowness and grayness), trash content (e.g., area and number of trash particles), leaf grade, and moisture content.

Another object is to cyclically press different fractions or segments of a cotton layer against an analyzer.

A further object is to provide analysis that may be employed to automatically or manually adjust ginning machine variables, so as to improve the final product.

A still further object is to provide portable and easily adaptable analysis equipment for any gin configuration.

Yet another object is to provide uniform cotton samples for grading.

An even further object is to provide color grade, trash grade, and moisture of cotton continuously as it is processed at a gin, without having to permanently remove it and maintain it separate from the remainder of the cotton.

A still further object is to immediately assess the value of cotton being processed in a gin, rather than the 5 to 14 day delay normally incurred in classing cotton with the U.S. Government grading system.

Another object is to provide a system that increases the accuracy and repeatability of cotton quality measurements.

An even still further object is to provide an apparatus for pressing or pressing/analyzing flowable solids other than a batt or layer of lint particles, such as flowable particulate material, including seeds, man-made fibers, pharmaceuticals, coal, and so forth, that are flowing across a wall, but are not necessarily compressible; wherein samples of the flowing material intermittently are pressed against at least part of the wall, which may be a window and which may constitute part of an analyzer capable of determining such properties as size, impurities, shape, color, moisture, and so forth. Depending upon the size of the particulates, the material does not necessarily essentially fill up the analysis window, with no voids, in the manner of the compressible layer of lint particles.

Other objects and advantages will be obvious from the following more detailed description of the invention in which FIG. 1 is a schematic view of the present invention.

FIGS. 4, 4a, and 4b, show different positions of the pressing means component of the analyzing means.

Figure 3:
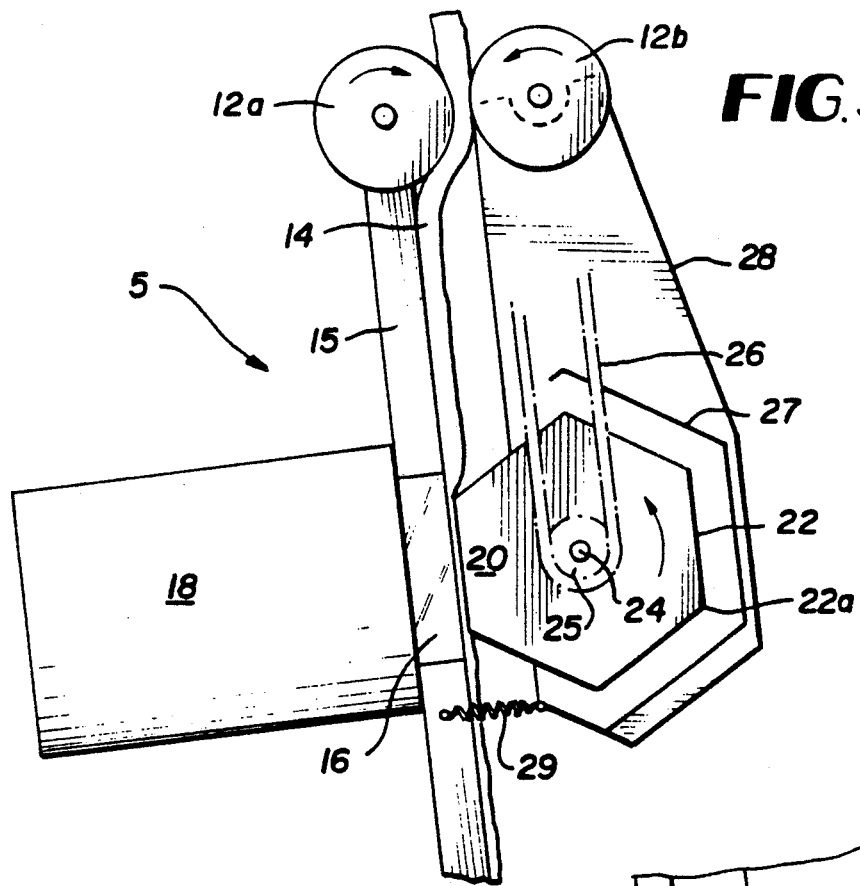
FIG. 3 illustrates components of a specific analyzing means.
Figure 5:
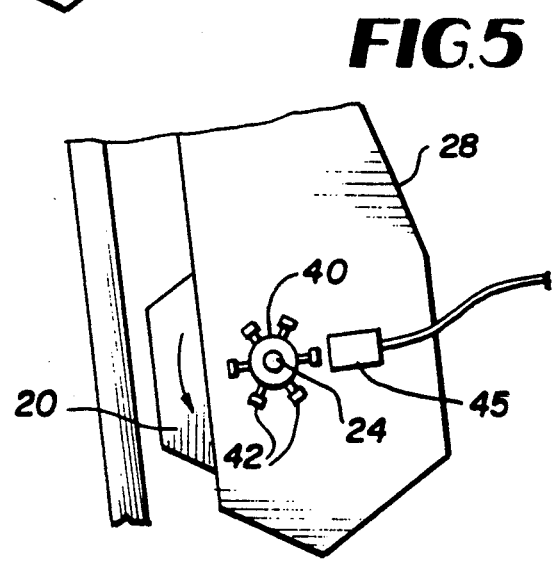

FIG. 5 illustrates additional elements of the pressing member element of FIG. 3.

Figure 6:
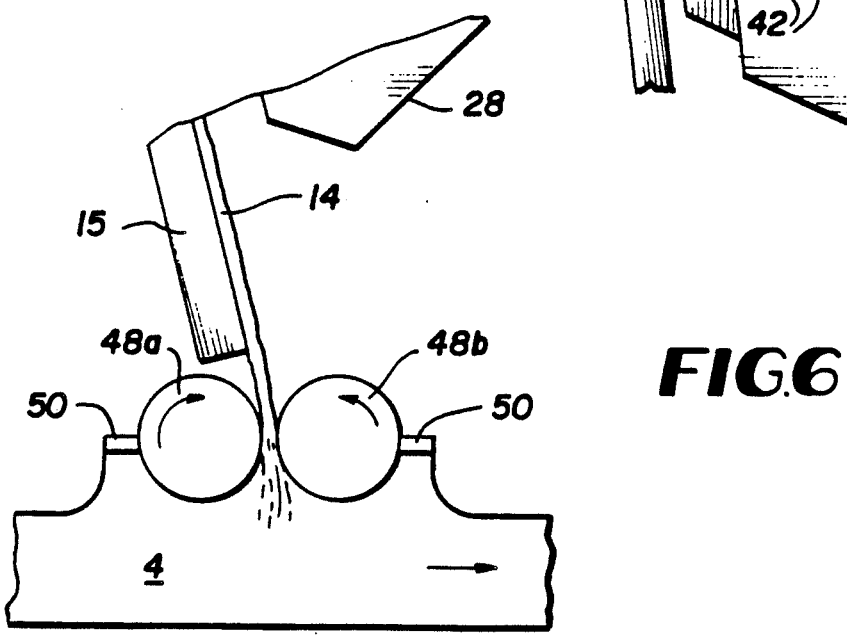

FIG. 6 shows means to disperse solids into the fluid stream that is returning to the main processing system.

Figure 2:
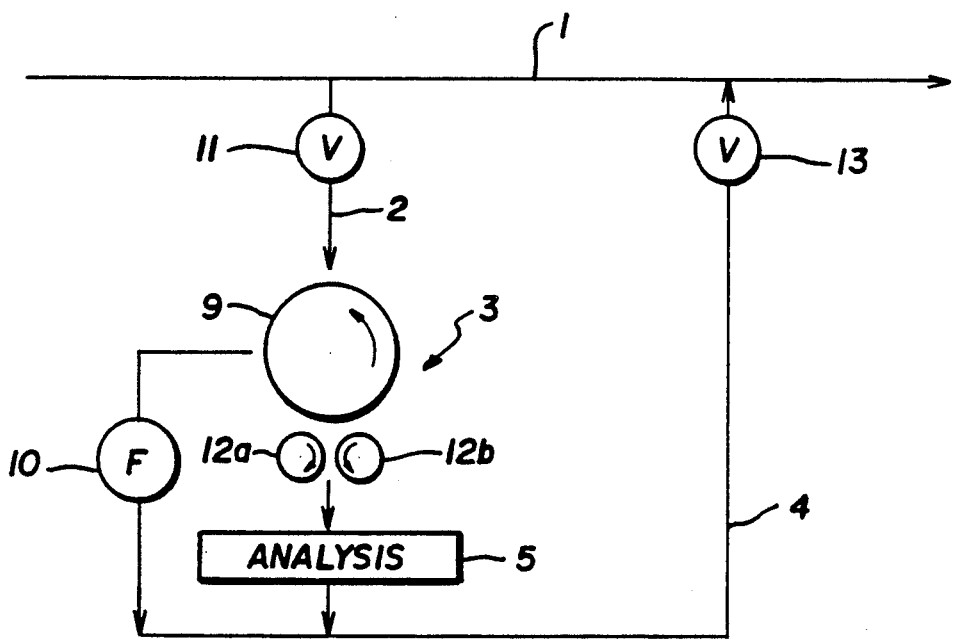
FIG. 2 is a schematic view in which an air-solids separating means is depicted.
Figure 7:
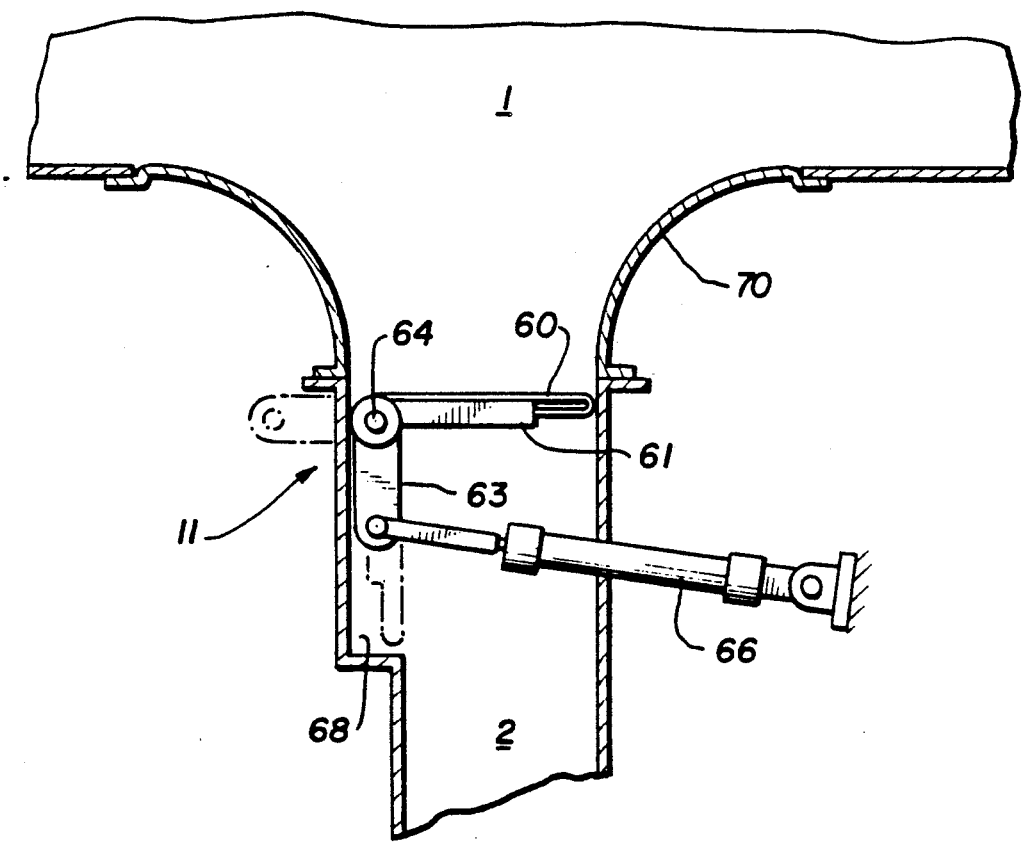

FIG. 7 is a partially sectional view of valve 11 in FIG. 2.

Figure 8:
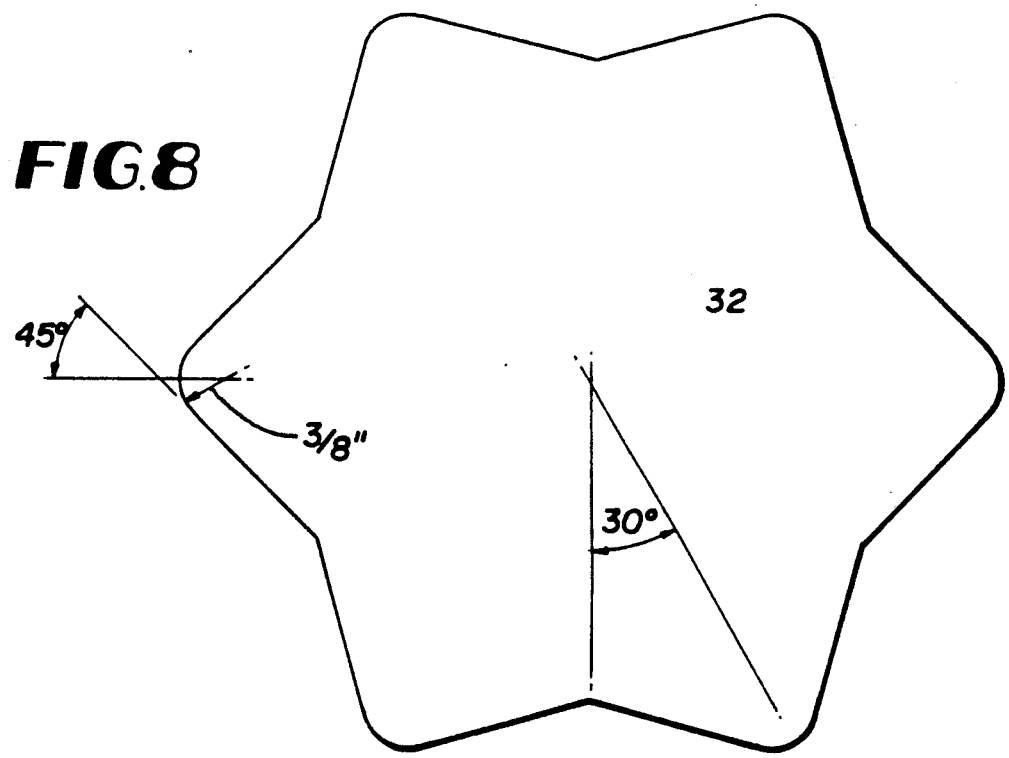

FIG. 8 is a view of the cam which helps to lift the pressing member element.

DETAILED DESCRIPTION

Figure 1:
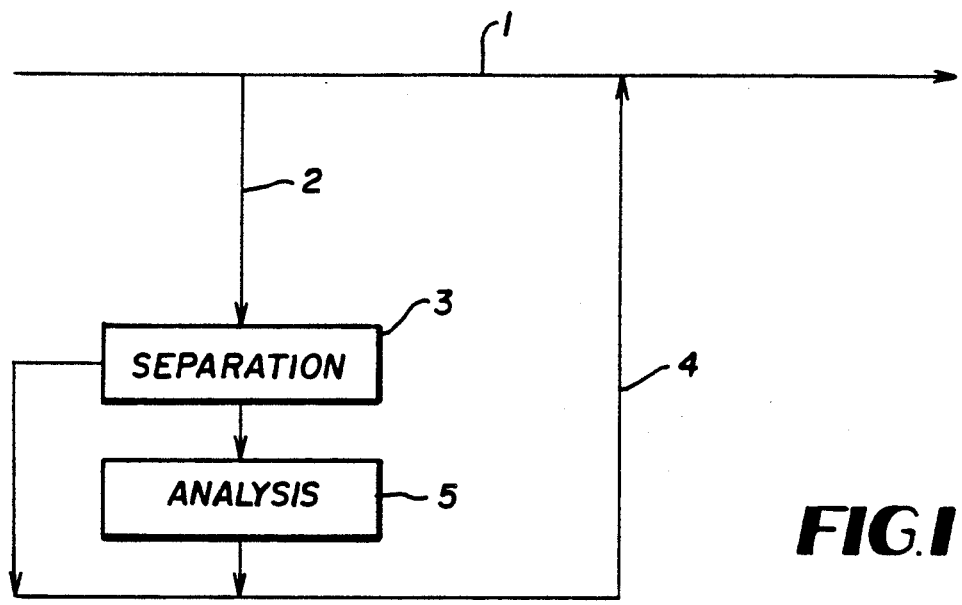

Referring to FIG. 1, reference numeral 1 designates a duct having fluid-entrained solids, such as air-entrained cotton lint, passing therethrough. The duct is part of an overall processing system for the solids, such as a cotton gin. A small portion or part of the fluid-entrained solids in duct 1 is diverted or extracted, continuously or intermittently, into by-pass conduit 2, which leads to a fluid-solid separation zone 3. Conventional fluid-solid separation techniques may be employed in the zone. Conduit 4 conveys separated fluid back to duct 1 downstream from the point of removal. Separated solids are sent to an analyzing zone 5 to determine such properties as color, moisture content, shape, size, and so forth, by means of analytical equipment known in the art. Thereafter, the solids are dispersed back into the fluid stream returning to duct 1.

FIG. 2 illustrates separation zone 3 in the case of an air-entrained stream of cotton lint. Such zone comprises a lint condenser cylinder 9 driven by a motor (not shown) that results in the formation of a batt on the cylinder. Although the condenser is of the same design as a conventional condenser (screen-type cylinderical wall) found in a gin, it is much smaller because much less material is passed therethrough. In accordance with prior art practices, condenser cylinder 9 preferably is driven by a variable-speed motor to provide uniform batt thickness by changing condenser speed. The speed may be changed manually in response to visual observations of the ginning rate, or automatically in response to pressure sensors in the ginning system that measure ginning rate fluctuations.

To bring lint cotton into the condenser through conduit 2 from duct 1, a suction fan 10 is provided in fluid-return conduit 4 connected to the downstream side of the condenser, that places a greater vacuum in the condenser than is found in duct 1. Preferably, the fan runs continuously; and a valve 11 in conduit 2 intermittently or continuously is opened, by means of a timer, to allow lint to be vacuumed into the condenser. Different vacuum times are required, depending upon the ginning rate, the size of duct 1, and the location of conduit 2 in the duct, in order to provide a predetermined amount of cotton to the condenser, for the purpose of producing a uniform batt thereon.

Doffing rollers 12a and 12b remove the batt from the lint condenser, partly compress the batt to densify it, and feed the densified batt to analyzing zone 5. The doffing rollers are driven by a chain and sprocket connection to the condenser cylinder 9, which is conventional in the prior art as to doffing rollers and condenser cylinders; and the rollers may be of the type ordinarily found in a gin, except that they are substantially smaller due to the relatively smaller amount of lint to be handled thereby. To help provide sealing means between the condenser and analyzing zone, preferably one of the doffing rollers is spring-loaded to allow variable batt thickness.

It can be seen from FIG. 2 that fan 10 is the means by which cotton and air are extracted from duct 1, and the means by which cotton and air are returned thereto via conduit 4. A valve 13, which preferably is a leaf valve, is provided in the downstream side of conduit 4, and is maintained in an open position whenever fan 10 is running, to enable cotton to be returned to duct 1 in a continuous manner.

FIG. 3 illustrates analyzing zone 5 in the case of analyzing a layer of flowable solids such as a cotton batt 14. A slanted wall or slide 15 is provided so that the batt slowly may slide down the wall by gravity, after being deposited thereon by means of condenser doffing rollers 12a and 12b.

A window or lens 16 is provided in at least part of the wall 15. An analyzer, schematically represented by reference numeral 18, is provided adjacent the window. Typically, the analyzer employs electromagnetic energy (e.g., light, infrared) to detect properties of the cotton, such as color, trash content and moisture content. Window or lens 16 is transparent to the extent to permit entry and reflection of electromagnetic rays of the analyzing devices. In lieu of inserting a window in wall 15, the analyzing instrument itself, i.e., the lens portion thereof, may be inserted into an opening or frame in wall 15. Typical window dimensions are 3 $\frac{1}{2}\times 4''$ glass, or 5"×6" frame for a video camera. For a camera analyzer, the opening usually is rectangular, while infrared meters are more readily accomodated by a circular opening. Rectangular resistance plates, e.g., 4"×6", may be employed for cotton moisture measurements, in lieu of a window.

If two different analyzers are employed in a side-by-side manner, then two side-by-side windows or openings may be provided in wall 15, as opposed to one large window.

Conventional analyzers known in the cotton analysis art may be employed in the practice of the present invention, and include video cameras for trash content analysis, as exemplified by the "Color/Trash Meter" made by Motion Control, Inc., and a similar device by Spinlab, Inc.; and infrared moisture sensors by Infrared Engineering, Inc., or Moisture Systems Corporation. These instruments previously have been employed to analyze cotton samples, remote from the cotton processing point.

If desired, electrical signals, in the case of a camera, may be transmitted from the camera to a multiple serial port device, each port of which accepts signals from a particular analyzer or sensor, to allow several serial computer signals to feed into a computer. Analog electrical signals from a moisture meter may be transmitted to an analog-to-digital converter, and then to a computer. Data files to document the quality of parameters may be created by recording each data signal. An additional data file may be created to produce a histogram as to a particular raw cotton source.

Analyzing zone 5 also includes pressing means for compressing cotton against the window. The size of the cotton layer being compressed or compacted thereagainst should be large enough to cover the window(s) 16.

Part of the pressing means is a cylinder 20 that, in cross section, is a polygon such as a hexagon, having a plurality of flat surfaces 22, wherein adjacent surfaces are joined together at juncture 22a. The cylinder includes a shaft 24, a sprocket 25 connected to one end of the shaft, and a chain 26 connected to sprocket 25 and to the sprocket of doffing roller 12b, so as to rotate cylinder 20.

Other parts of the pressing means are represented by reference numeral 27 which designates an inner shroud around cylinder 20, while an outer shroud connected to the inner shroud is designated by numeral 28. Shaft 24 of cylinder 20 is journalled for rotation in the outer shroud, whereby such shroud provides support means for the cylinder. Part of the function of inner shroud 27 is to help to hold the sides of the outer shroud together, provide an additional safety shield, and prevent contamination of the particulates or batt being compressed.

Outer shroud 28 is pivotally connected to the shaft of doffing roller 12b, so that the pressing means (shrouds plus cylinder 20) are movable with respect to wall 15. Pressure against the batt 14 on wall 15 adjacent window 16 essentially is provided by the combined mass or weight of the cylinder (shaft, sprocket, and so forth) and its support means, as expressed against the batt through a vector normal to the surface of wall 15.

In some cases, pressure may be provided by tension springs 29 connected between the wall 15 and outer shroud 28 at one or more points.

Referring now to FIG. 4, connected to one end of cylinder shaft 24, to rotate therewith, is a multi-lobed cam 30. The number of lobes on the cam is equal to the number of flat surfaces 22 on cylinder 20. A cam engagement member 32, such as a roller bearing, is connected to wall 15 by means of bracket 34. The cam is positioned on the cylinder shaft 24 so that, during rotation thereof, one of the valleys between adjacent cam lobes is in contact with the cam engagement member 32 when a flat surface 22 of cylinder 20 is in pressing, substantially parallel engagement with the batt on wall 15.

As shown in FIG. 4a, as cylinder 20 is lifted off the batt, it slowly rotates until one of the junctures 22a between adjacent faces 22 propels the batt from the window, so that a new batt segment may displace the previously analyzed segment. To assist such propelling or sweeping, juncture 22a may include spaced-apart rivets (not shown) along the length of the juncture. In the absence of such sweeping action by juncture 22a, the batt tends to accordion, because it partly clings to slide 15, due to electrostatic forces and, perhaps, other phenomena. Many particulates do not present this clinging problem, depending upon the angle of slide 15, whereby, in these latter instances, pressing member or cylinder 20 need not be rotational and multi-sided, but simply periodically may be lifted off the particulates by a multi-lobed, rotating cam, such as cam 30.

As shown in FIG. 4b, when the apex of a cam lobe contacts the cam engagement member 32, cylinder 20 completely is lifted off the batt.

As the cam continues to rotate, along with cylinder 20, to another lobe valley adjacent to cam engagement member 32, the cylinder and accompanying support means naturally swing back against the wall from their offset pivot point on duffer roller 12b, as illustrated in FIG. 4, to compress a new segment of batt 14. against another face of cylinder 20. As can be seen, the cylinder is disposed to bear against the wall or batt whenever it is not in a lifted position.

In a typical operation, the cotton layer or batt 14 is forced to pause for a brief period, usually less than a second, for analysis. This pause may be effected by providing a cam engagement member 32 that has a diameter that is too large to follow the contour of the valley in the cam, whereby the compression cylinder, while slowly rotating, hesitates a moment before beginning to lift off the batt, as the cam engagement member passes through each cam valley.

Referring to FIG. 5, a rotating collar member 40 also is attached to an end of cylinder shaft 24. It may be similar to multi-lobed cam 30, or it may have a series of bolts or other projections 42 threaded into or otherwise secured to the periphery thereof, equally spaced from one another, equal in number to the flat surfaces 22 on cylinder 20. In conjunction with collar 40 is a proximity (photocell) switch 45 mounted on outer shroud 28. Switch 45 is connected to analyzer 18 to activate same.

In operation, each time a bolt 42 on collar 40 passes by the proximity switch 40, the analyzer is activated. Collar 40 is positioned on cylinder shaft 24 so that the analyzer is activated only when a flat surface 22 of cylinder 20 is in pressing, substantially parallel engagement with the cotton layer 14 on wall 15.

Referring now to FIG. 6, after analysis, doffing rollers 48a and 48b remove the batt from wall 15, break it up, and disperse cotton lint into the air stream in conduit 4 returning to duct 1. These rollers, which may be of the same design and generally the same size as doffing rollers 12a and 12b, are set closely adjacent one another so as to provide an air seal upstream of the rollers, in conjunction with peripheral felt seals 50, when the batt passes therebetween, to prevent air from being blown into the bottom of the slide 15, as well as to meter the lint batt into the air stream. To help provide such sealing means, preferably one of the slide doffing rollers is spring-loaded to allow variable batt thickness.

Referring now to FIG. 7, therein is illustrated a preferred design of value 11 in conduit 2, that allows cotton to pass to separation zone 3 and analyzing zone 5 (see FIG. 1 or 2). The valve comprises a leaf valve fabricated from sheet metal 60 folded upon itself at one end, and anchored to a metal plate 61 at its other end. Plate 61 is secured to transverse member 63 for rotation around shaft 64 by means of a solenoid activated piston 66, so that sheet 60 and plate 61 may be moved into recessed area 68 in conduit 2 in order to provide communication between conduit 2 and duct 1. In order to expedite the flow of entrained lint past the leaf valve into conduit 2, an air-foil shaped connector 70 is provided between duct 1 and conduit 2. The radius of curvature of the air-foil preferably is about 6", but may be as low as 3".

In addition to analyzing cotton for trash or moisture, the present invention may be employed to determine the diameter of cotton fibers, entanglement of fibers (neps), relative maturities of fibers, different kinds of impurities such as plant parts or soil particles, as well as dimensions of impurities. The invention also is suitable for pressing or pressing/analyzing other flowable solids.

With particular regard to cotton, the combination of the slanted wall and the multi-sided compression cylinder is a separate, stand-alone apparatus that may be moved from one gin to another, where it may be employed to remove seed cotton or lint cotton from conveying ducts, classifying the cotton by various components such as moisture, trash, and color, and thereafter returning that cotton to the conveying duct in the gin.

Only the multi-sided compression cylinder may be required in those situations where a gin already includes the step of (a) forming batts of cotton by means of a condenser and (b) thereafter sliding the batts down an inclined slide into a bale press. In this latter case, an analyzing or sensing device may be installed in the slide by cutting a hole in the underside thereof, and installing a narrow multi-sided compression cylinder opposite same.

Other types of analyzers, which do not require a window lens in the wall surface, may be employed in the present invention. For example, that part of the wall surface on which the cotton is compressed may include electrode sensors that detect moisture.

While wall or slide 15 is illustrated as being substantially vertically with regard to analyzing a cotton batt, in many instances it may be necessary for the wall to be substantially horizontal when treating readily flowable solid particulates, so that the wall functions in the manner of a gently inclined ramp.

Dimensions, parameters and shapes of one exemplary embodiment of the present invention, suitable for compressing a lint batt formed from entrained lint extracted from a 30"×30" duct in a cotton gin, are as follows:

diameter of flue that delivers entrained lint to lint condenser=7"
capacity of fan that delivers entrained lint to the lint condenser, and later returns analyzed cotton to the gin duct=900 ft$^3$/minute
speed of lint condenser=6.7 rpm
diameter of lint condenser=17"
length of lint condenser=11"
motor for condenser=¾ hp, variable speed motor, 492 in-lb of output torque that has an output speed of 69 rpm. Motor set to turn at 12 rpm
speed of condenser doffing roller=23 rpm
diameter of condenser doffing roller=4", fluted ⅛"×⅛", spaced 3/16" apart
length of condenser doffing roller=11"
diameter of compression cylinder, hexagonal shape, from face 16 to opposite face 16=10.75"; from juncture 16a to opposite juncture 16a=12"
length of compression cylinder=12"
speed of compression cylinder=11 rpm
width of each face 16 on compression cylinder=5"
pressure of compression cylinder on lint batt=about 1 psig
combined weight of compression cylinder, drive shaft and shrouds=80#
cam speed=11 rpm
minimum diameter of cam (valley to valley)=4⅝"
maximum diameter of cam (apex to apex)=6"
cam lobe shape and dimension=see FIG. 8
outside diameter of idler roller bearing for cam to ride on =1 3/16"
pause time of compression cylinder =0.8 seconds effected by cam and idler roller bearing
density, thickness of lint batt on slide, before analysis =0.3 pounds per ft$^3$, about 1-3 inches thick
angle of slide 17 =75° from horizontal
width of slide =12½"
length of slide =25"
diameter of slide doffing rollers =5¼", steel, fluted (rectangular grooves cut into the length of the rollers, ⅛"×⅛", spaced ¾" apart)
length of slide doffing rollers =12½"
speed of slide doffing rollers =26 rpm
diameter of return conduit =7"

These parameters only are exemplary. Much higher compression may be employed. The relationship of speeds of rotation of the various components usually is more important than the actual speeds. As an example, while the components may revolve faster or slower, the slide doffing rollers most preferably should not turn slower than the condenser doffing rollers.

We claim:

1. Apparatus for analyzing fluid-entrained solids passing through a duct comprising
   a. a by-pass conduit connected to said duct to remove a fluid stream containing a small part of the solids in said duct;
   b. separating means connected to said by-pass conduit to separate said fluid stream into a solids fraction and a fluid stream that is essentially free of said solids;
   c. a return conduit connected to said separating means to direct said essentially solids-free fluid stream back to said duct downstream from said by-pass means;
   d. analyzing means connected to said separating means to analyze said solids fraction; and
   e. dispersing means connected to said return conduit and said analyzing means to disperse solids, after analysis, into said fluid stream in said return conduit.

2. The apparatus of claim 1 wherein said fluid is air, wherein said solids are lint cotton, wherein said separating means comprises a lint condenser that forms a batt from said lint removed from said duct; wherein said analyzing means comprises means to compress said batt, and means to analyze said batt, when compressed, for at least one property selected from the group consisting of color, trash content, leaf grade, and moisture content.

3. The apparatus of claim 1 wherein said analyzing means comprises:
   a. a wall adjacent said separating means, said wall having a pressing zone thereon;
   b. means to pass said separated solids fraction in contact with said wall;
   c. means to press a segment of said solids fraction against said wall in said pressing zone; wherein said pressing means comprises
      i. a member having at least one surface that conforms to the shape of said wall so as to be able to lie in pressing engagement with said segment of said solids fraction;
      ii. means to lift said member off said segment to permit another segment of said solids fraction to displace said first segment in said pressing zone, and means to release said lifting means to permit said member to press against said another segment of said solids fraction in said pressing zone; and
   d. a solids analyzer adjacent said pressing zone that analyzes each of said pressed segments.

4. The apparatus of claim 3 further including means to cyclically lift said member, and to cyclically release said lifting means so as to provide for cyclical pressure on a plurality of segments of said solids fraction.

5. The apparatus of claim 4 wherein said lifting and lifting release means comprises a rotatable lobed cam connected to said member; cam-engaging means positioned at a fixed distance from said wall; wherein said member is lifted each time a lobe of said cam contacts said cam-engaging means.

6. The apparatus of claim 4 wherein said wall and said surface of said member both are flat.

7. The apparatus of claim 6 wherein said member comprises an elongated cylinder that is polygonal in cross-section, so that it includes a plurality of flat surfaces, wherein a different one of said surfaces engages said solids fraction during any two successive pressurizations.

8. The apparatus of claim 7 further including means to rotate said cylinder about its axis; and wherein said lifting and lifting release means comprises a multi-lobed cam connected to said cylinder that rotates therewith, said cam having the same number of lobes as the number of flat surfaces on said cylinder; cam-engaging means positioned at a fixed distance from said wall; wherein said cylinder is lifted each time one of said cam lobes contacts said cam-engaging means.

9. The apparatus of claim 8 wherein said wall is positioned so that said solids fraction slowly slides down said wall by gravity.

10. The apparatus of claim 9 further including switch means connected to said solids analyzer to activate same; a switch activator connected to said cylinder that rotates therewith, said switch activator having a plurality of projections one of which activates said switch means each time a surface of said cylinder is in pressing engagement with said solids fraction.

11. The apparatus of claim 9 wherein said fluid is air, wherein said solids are lint cotton, wherein said separating means comprises a lint condenser that forms a batt from said lint cotton; and wherein said solids analyzer comprises means to analyze said batt for at least one property selected from the group consisting of color, trash content, leaf grade, and moisture content.

12. The apparatus of claim 11 wherein said dispersing means comprises means to break up said batt into lint particles, and to disperse said particles into said return conduit.

13. A process for analyzing fluid-entrained solids passing through a duct comprising
 a. removing from said duct a fluid stream containing a small part of said solids in said duct;
 b. separating said fluid stream into a solids fraction and a fluid stream essentially free of said solids;
 c. returning said essentially solids-free fluid stream to said duct downstream from the point of removal;
 d. analyzing said solids fraction; and
 e. dispersing solids, after analysis, into said fluid stream being returned to said duct.

14. The process of claim 13 wherein said fluid stream is air; wherein said solids are cotton lint; wherein said separating step comprises forming said lint fraction into a batt; wherein said analyzing step comprises compressing said batt, and analyzing said batt, when compressed, for at least one property selected from the group consisting of color, trash content, leaf grade, and moisture content.

15. The process of claim 13 wherein said analyzing step comprises:
 a. passing a layer of said solids fraction in contact with a wall having a pressing zone thereon;
 b. pressing a segment of said layer against said wall in said pressing zone, wherein said step of pressing comprises placing a weighted object against said segment;
 c. analyzing said segment when said object is placed thereagainst;
 d. terminating said analyzing step, and lifting said object off said segment;
 e. displacing said segment with another segment of said solids fraction; and
 f. repeating said pressing, analyzing and lifting steps with said another segment.

16. The process of claim 15 wherein the steps of compressing, analyzing and lifting are carried out in a cyclical manner on a series of segments.

17. The process of claim 16 wherein said wall is positioned so that said solids fraction slides down said wall by gravity.

18. The process of claim 17 wherein said layer is a batt of cotton lint, wherein said compression is sufficient so that said segment presents a face of uniform cotton density against said wall in said pressing zone.

19. The process of claim 18 further including forming said batt by condensing entrained lint cotton in an air stream into a batt.

* * * * *